United States Patent
Chandra et al.

(10) Patent No.: US 8,363,779 B2
(45) Date of Patent: Jan. 29, 2013

(54) SYSTEM AND METHOD OF ACQUIRING MULTI-ENERGY CT IMAGING DATA

(75) Inventors: Naveen Chandra, Waukesha, WI (US); Xiaoye Wu, Rexford, NY (US); Thomas L. Toth, Brookfield, WI (US); Jiang Hsieh, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 13/484,707

(22) Filed: May 31, 2012

(65) Prior Publication Data
US 2012/0236984 A1  Sep. 20, 2012

Related U.S. Application Data

(63) Continuation of application No. 12/760,862, filed on Apr. 15, 2010, now Pat. No. 8,199,875, which is a continuation-in-part of application No. 12/635,901, filed on Dec. 11, 2009, now Pat. No. 8,199,874.

(51) Int. Cl.
*A61B 6/00* (2006.01)
*H05G 1/64* (2006.01)
*G06K 9/00* (2006.01)

(52) U.S. Cl. ....... 378/16; 378/98.9; 378/98.12; 382/130

(58) Field of Classification Search .................. 378/4, 5, 378/16, 98.9, 98.11, 98.12; 382/130, 131
See application file for complete search history.

(56) References Cited

U.S. PATENT DOCUMENTS

| | | | |
|---|---|---|---|
| 4,541,106 A | 9/1985 | Belanger et al. | |
| 4,780,897 A | 10/1988 | McDaniel et al. | |
| 6,343,112 B1 | 1/2002 | Petrick et al. | |
| 6,393,097 B1 | 5/2002 | Aufrichtig et al. | |
| 6,621,887 B2 | 9/2003 | Albagli et al. | |
| 6,931,098 B2 | 8/2005 | Kump et al. | |
| 7,054,407 B1 | 5/2006 | Li et al. | |
| 7,209,537 B2 | 4/2007 | Popescu | |
| 7,711,082 B2 | 5/2010 | Fujimoto et al. | |
| 2006/0030768 A1* | 2/2006 | Ramamurthy et al. | 600/407 |
| 2006/0109951 A1* | 5/2006 | Popescu | 378/4 |
| 2007/0242795 A1 | 10/2007 | Bernhardt | |
| 2008/0144764 A1* | 6/2008 | Nishide et al. | 378/5 |
| 2008/0317196 A1* | 12/2008 | Imai et al. | 378/8 |
| 2009/0097611 A1 | 4/2009 | Nishide et al. | |
| 2009/0180585 A1 | 7/2009 | Fujimoto et al. | |
| 2010/0034343 A1* | 2/2010 | Akino | 378/15 |
| 2011/0052022 A1 | 3/2011 | Xu et al. | |

FOREIGN PATENT DOCUMENTS
EP  1734405 A2  12/2006
EP  1980207 A1  10/2008

* cited by examiner

*Primary Examiner* — Alexander H Taningco
(74) *Attorney, Agent, or Firm* — Ziolkowski Patent Solutions Group, SC (57) ABSTRACT

A CT system includes a rotatable gantry having an opening for receiving an object to be scanned, and a controller. The controller is configured to apply a first kVp for a first time period, apply a second kVp for a second time period, integrate two or more view datasets during the first time period, integrate one or more view datasets during the second time period, and generate an image using the datasets integrated during the first time period and during the second time period.

20 Claims, 10 Drawing Sheets

SYSTEM AND METHOD OF ACQUIRING MULTI-ENERGY CT IMAGING DATA

CROSS-REFERENCE TO RELATED APPLICATIONS

The present application is a continuation of and claims priority to U.S. patent application Ser. No. 12/760,862 filed Apr. 15, 2010, which is a continuation-in-part of and claims priority to U.S. patent application Ser. No. 12/635,901 filed Dec. 11, 2009, the disclosures of which are incorporated herein.

BACKGROUND OF THE INVENTION

Embodiments of the invention relate generally to diagnostic imaging and, more particularly, to an apparatus and method of improving noise in multi-energy CT imaging applications.

Typically, in computed tomography (CT) imaging systems, an x-ray source emits a fan-shaped or cone-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis, which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom. Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

A CT imaging system may include an energy sensitive (ES), multi-energy (ME), and/or dual-energy (DE) CT imaging system that may be referred to as an ESCT, MECT, and/or DECT imaging system, in order to acquire data for material decomposition or effective Z or monochromatic image estimation. ESCT/MECT/DECT provides energy discrimination. For example, in the absence of object scatter, the system derives the material attenuation at a different energy based on the signal from two relative regions of photon energy from the spectrum: the low-energy and the high-energy portions of the incident x-ray spectrum. In a given energy region relevant to medical CT, two physical processes dominate the x-ray attenuation: (1) Compton scatter and the (2) photoelectric effect. These two processes are sensitive to the photon energy and hence each of the atomic elements has a unique energy sensitive attenuation signature. Therefore, the detected signals from two energy regions provide sufficient information to resolve the energy dependence of the material being imaged. Furthermore, detected signals from the two energy regions provide sufficient information to determine material attenuation coefficients in terms of Compton scatter and photoelectric effect. Alternatively, the material attenuation may be expressed as the relative composition of an object composed of two hypothetical materials, or the density and effective atomic number with the scanned object. As understood in the art, using a mathematical change of basis, energy sensitive attenuation can be expressed in terms of two base materials, densities, effective Z number, or as two monochromatic representations having different keV.

Such systems may use a direct conversion detector material in lieu of a scintillator. One of the ESCT, MECT, and/or DECT imaging systems in an example is configured to be responsive to different x-ray spectra. Energy sensitive detectors may be used such that each x-ray photon reaching the detector is recorded with its photon energy. One technique to acquire projection data for material decomposition includes using energy sensitive detectors, such as a CZT or other direct conversion material having electronically pixelated structures or anodes attached thereto. However, such systems typically include additional cost and complexity of operation in order separate and distinguish energy content of each received x-ray photon.

In an alternative, a conventional scintillator-based third-generation CT system may be used to provide energy sensitive measurements. Such systems may acquire projections sequentially at different peak kilovoltage (kVp) operating levels of the x-ray tube, which changes the peak and spectrum of energy of the incident photons comprising the emitted x-ray beams. A principle objective of scanning with two distinctive energy spectra is to obtain diagnostic CT images that enhance information (contrast separation, material specificity, etc.) within the image by utilizing two scans at different polychromatic energy states.

One technique has been proposed to achieve energy sensitive scanning including acquiring two scans at, for instance, 80 kVp and 140 kVp. The two scans may be obtained (1) back-to-back sequentially in time where the scans require two rotations of the gantry around the subject that may be hundreds of milliseconds to seconds apart, (2) interleaved as a function of the rotation angle requiring one rotation around the subject, or (3) using a two tube/two detector system with the tubes/detectors mounted ~90 degrees apart, as examples.

High frequency, low capacitance generators have made it possible to switch the kVp potential of the high frequency electromagnetic energy projection source on alternating views and interleave datasets. As a result, data for two energy sensitive scans may be obtained in a temporally interleaved fashion rather than with separate scans made several seconds apart or with a two tube/two detector system. In order to improve contrast and reduce or eliminate beam hardening artifacts, it is desirable to increase energy separation between high and low kVp scans. Energy separation may be increased by increasing energy in high kVp scans. However, high kVp scans may be limited due to system stability at high voltage.

Alternatively, energy separation may be increased by decreasing energy in low kVp scans. However, x-ray attenuation may occur for low kVp projections to the extent that system noise may swamp a received signal, and x-ray attenuation typically increases as the size of the imaging object increases. As may be experienced in conventional single kVp imaging, imaging of some objects at, for instance, up to 120 kVp can cause projection data to be contaminated as detected signals become so weak that they are swamped out by other interfering signals such as electronic system noise and scattered x-ray noise. This can result in a decreased signal-to-noise ratio (SNR). Thus, poor SNR may result from electronic noise, which may be mitigated, to an extent, by increasing energy separation between the low and high kVp scans, as an example.

However, there is a limit below which it may not be advantageous to obtain low kVp data. A low signal threshold may be determined below which signals may be corrupted. The low signal threshold may be based on, for instance, geometric factors related to the imaging system and other imaging parameters. Typically, the low signal threshold is determined and used to establish the low kVp energy level Thus, SNR and other imaging characteristics may be improved by increasing energy separation between high and low kVp scans. However, although energy separation may be increased by directing the generator to apply a greater high kVp energy and to apply a lesser low kVp energy, the overall benefits may be limited because of high voltage stability issues on the high kVp end and because of electronic and other noise on the low kVp end. Thus, there is a need to decrease noise in multi-energy imaging applications.

Therefore, it would be desirable to have a system and method of obtaining multi-energy imaging data having reduced noise therein.

BRIEF DESCRIPTION OF THE INVENTION

Embodiments of the invention are directed to a method and apparatus for obtaining imaging data having reduced noise therein.

According to an aspect of the invention, a CT system includes a rotatable gantry having an opening for receiving an object to be scanned, and a controller configured to apply a first kVp for a first time period, apply a second kVp for a second time period, wherein the second time period is different from the first time period, acquire a first asymmetric view dataset during at least a portion of the first time period, acquire a second asymmetric view dataset during at least a portion of the second time period, and generate an image using the acquired first and second asymmetric view datasets.

According to another aspect of the invention, a method of imaging includes selecting a rise time skew period based on characteristics of a generator, selecting a fall time skew period, different from the rise time skew period, based on characteristics of the generator, triggering acquisition of a low kVp dataset during a first timeframe and based on the fall time skew period, triggering acquisition of a high kVp dataset during a second timeframe and based on the rise time skew period, wherein the first timeframe is a time duration that is greater than a time duration of the second timeframe, and generating an image using at least the acquired low kVp dataset and the acquired high kVp dataset.

According to yet another aspect of the invention, a computer readable storage medium having a computer program stored thereon and representing a set of instructions that when executed by a computer causes the computer to optimize an energy separation between imaging data to be acquired at a first energy level and imaging data to be acquired at a second energy level, the optimization based on a rise time characteristic and a fall time characteristic of a generator, acquire a first view of imaging data for at least a portion of a first time period while the first energy level is applied to an imaging source by the generator, acquire a second view of imaging data for at least a portion of a second time period while the second energy level is applied to the imaging source by the generator, and generate an image using the acquired first view of imaging data and the acquired second view of imaging data.

These and other advantages and features will be more readily understood from the following detailed description of preferred embodiments of the invention that is provided in connection with the accompanying drawings.

DETAILED DESCRIPTION

Diagnostics devices comprise x-ray systems, magnetic resonance (MR) systems, ultrasound systems, computed tomography (CT) systems, positron emission tomography (PET) systems, ultrasound, nuclear medicine, and other types of imaging systems. Applications of x-ray sources comprise imaging, medical, security, and industrial inspection applications. However, it will be appreciated by those skilled in the art that an implementation is applicable for use with single-slice or other multi-slice configurations. Moreover, an implementation is employable for the detection and conversion of x-rays. However, one skilled in the art will further appreciate that an implementation is employable for the detection and conversion of other high frequency electromagnetic energy. An implementation is employable with a "third generation" CT scanner and/or other CT systems.

The operating environment of the invention is described with respect to a sixty-four-slice computed tomography (CT) system. However, it will be appreciated by those skilled in the art that the invention is equally applicable for use with other multi-slice configurations, and with systems having a capability of shifting, or "wobbling" the focal spot during operation. Moreover, the invention will be described with respect to the detection and conversion of x-rays. However, one skilled in the art will further appreciate that the invention is equally applicable for the detection and conversion of other high frequency electromagnetic energy. The invention will be described with respect to a "third generation" CT scanner, but is equally applicable with other CT systems.

A dual energy CT system and method is disclosed. Embodiments of the invention support the acquisition of both anatomical detail as well as tissue characterization information for medical CT, and for components within luggage. Energy discriminatory information or data may be used to reduce the effects of beam hardening and the like. The system supports the acquisition of tissue discriminatory data and therefore provides diagnostic information that is indicative of disease or other pathologies. This detector can also be used to detect, measure, and characterize materials that may be injected into the subject such as contrast agents and other specialized materials by the use of optimal energy weighting to boost the contrast of iodine and calcium (and other high atomic or materials). Contrast agents can, for example, include iodine that is injected into the blood stream for better visualization. For baggage scanning, the effective atomic number generated from energy sensitive CT principles allows reduction in image artifacts, such as beam hardening, as well as provides addition discriminatory information for false alarm reduction.

Figure 1:
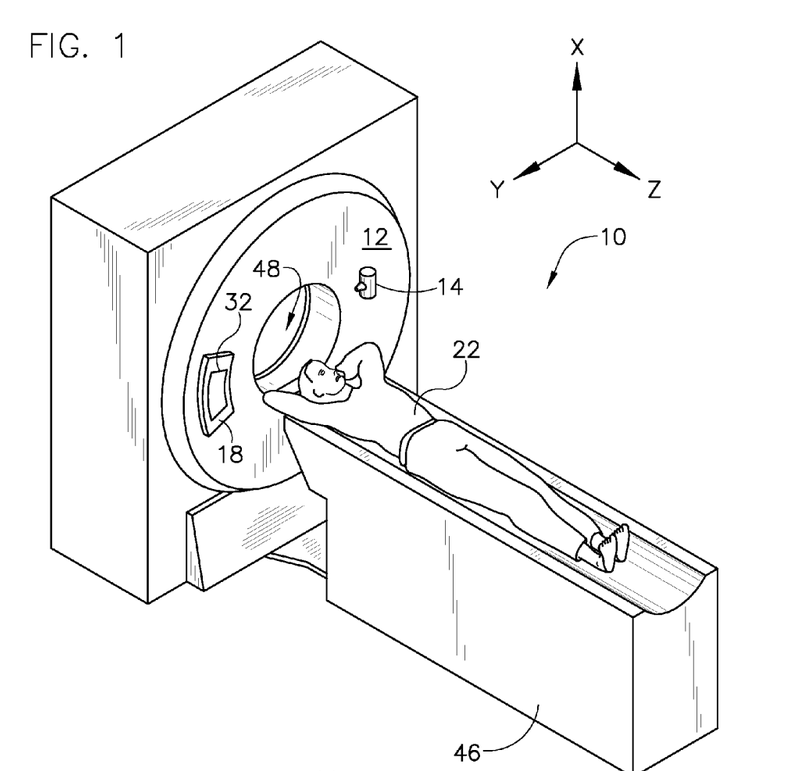
FIG. 1 is a pictorial view of a CT imaging system.
Figure 2:
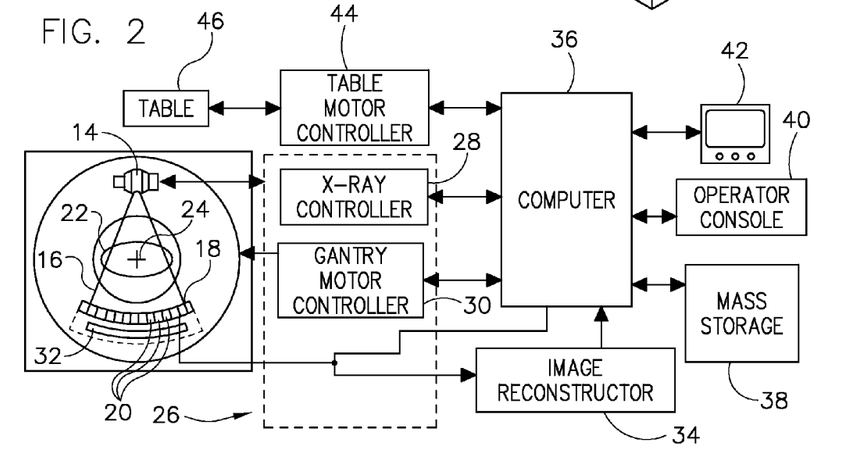
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector assembly 18 that includes a collimator on the opposite side of the gantry 12. In embodiments of the invention, x-ray source 14 includes either a stationary target or a rotating target. Detector assembly 18 is formed by a plurality of detectors 20 and data acquisition systems (DAS) 32. The plurality of detectors 20 sense the projected x-rays that pass through a medical patient 22, and DAS 32 converts the data to digital signals for subsequent processing. Each detector 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 and generator 29 that provides power and timing signals to x-ray source 14 and a gantry motor controller 30 that controls the rotational speed and position of gantry 12. An image reconstructor 34 receives sampled and digitized x-ray data from DAS 32 and performs high speed reconstruction. The reconstructed image and the embodiments described herein are applied as an input to a computer 36 which stores the image in a mass storage device 38, which may include computer RAM, discs, and the like.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves patients 22 through a gantry opening 48 of FIG. 1 in whole or in part.

System 10 may be operated in either monopolar or bipolar modes. In monopolar operation, either the anode is grounded and a negative potential is applied to the cathode, or the cathode is grounded and a positive potential is applied to the anode. Conversely, in bipolar operation, an applied potential is split between the anode and the cathode. In either case, monopolar or bipolar, a potential is applied between the anode and cathode, and electrons emitting from the cathode are caused to accelerate, via the potential, toward the anode. When, for instance, a −140 kV voltage differential is maintained between the cathode and the anode and the tube is a bipolar design, the cathode may be maintained at, for instance, −70 kV, and the anode may be maintained at +70 kV. In contrast, for a monopolar design having likewise a −140 kV standoff between the cathode and the anode, the cathode accordingly is maintained at this higher potential of −140 kV while the anode is grounded and thus maintained at approximately 0 kV. Accordingly, the anode is operated having a net 140 kV difference with the cathode within the tube.

Figure 3:
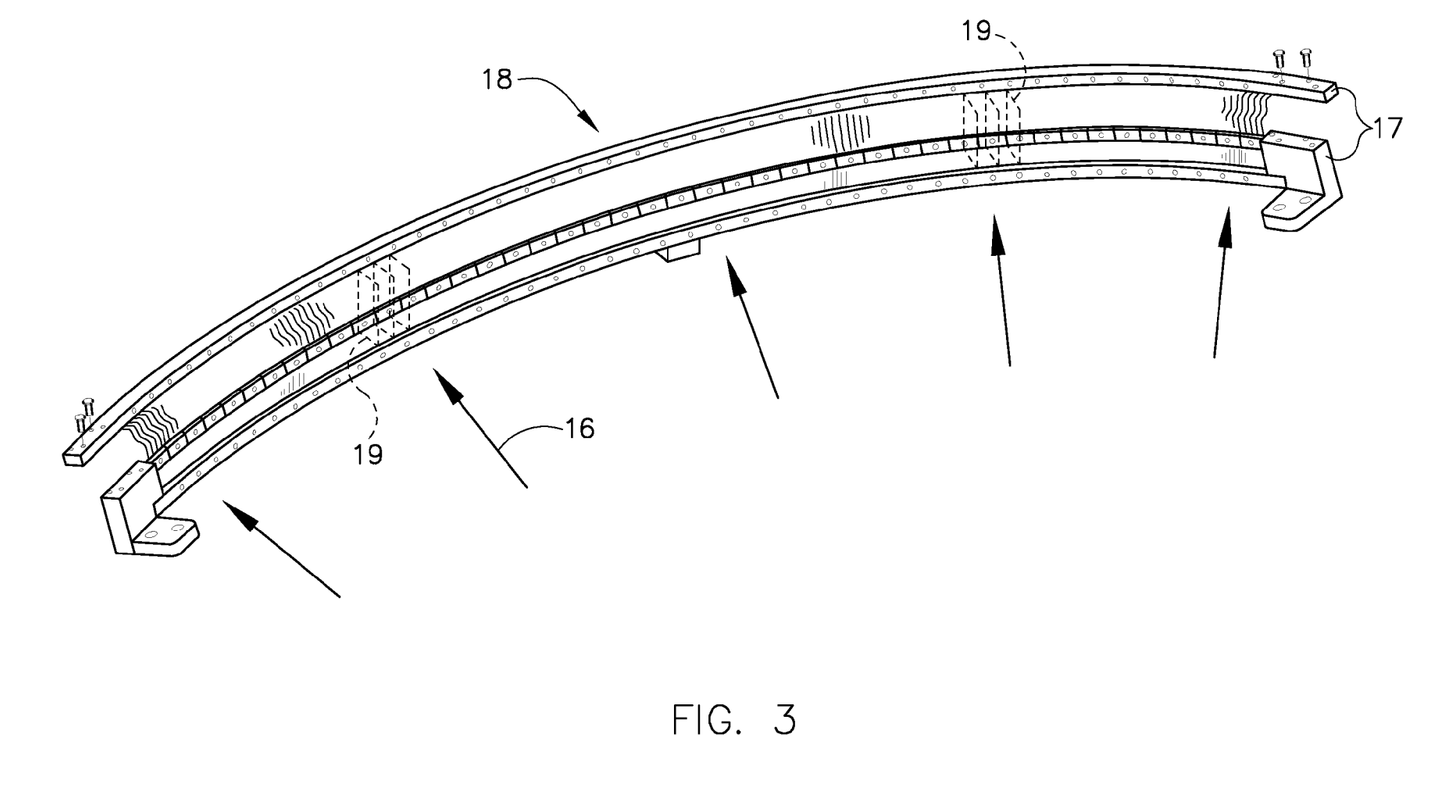
FIG. 3 is a perspective view of one embodiment of a CT system detector array.

As shown in FIG. 3, detector assembly 18 includes rails 17 having collimating blades or plates 19 placed therebetween. Plates 19 are positioned to collimate x-rays 16 before such beams impinge upon, for instance, detector 20 of FIG. 4 positioned on detector assembly 18. In one embodiment, detector assembly 18 includes 57 detectors 20, such as will be illustrated, each detector 20 having an array size of 64×16 of pixel elements 50. As a result, detector assembly 18 has 64 rows and 912 columns (16×57 detectors) which allows 64 simultaneous slices of data to be collected with each rotation of gantry 12.

Figure 4:
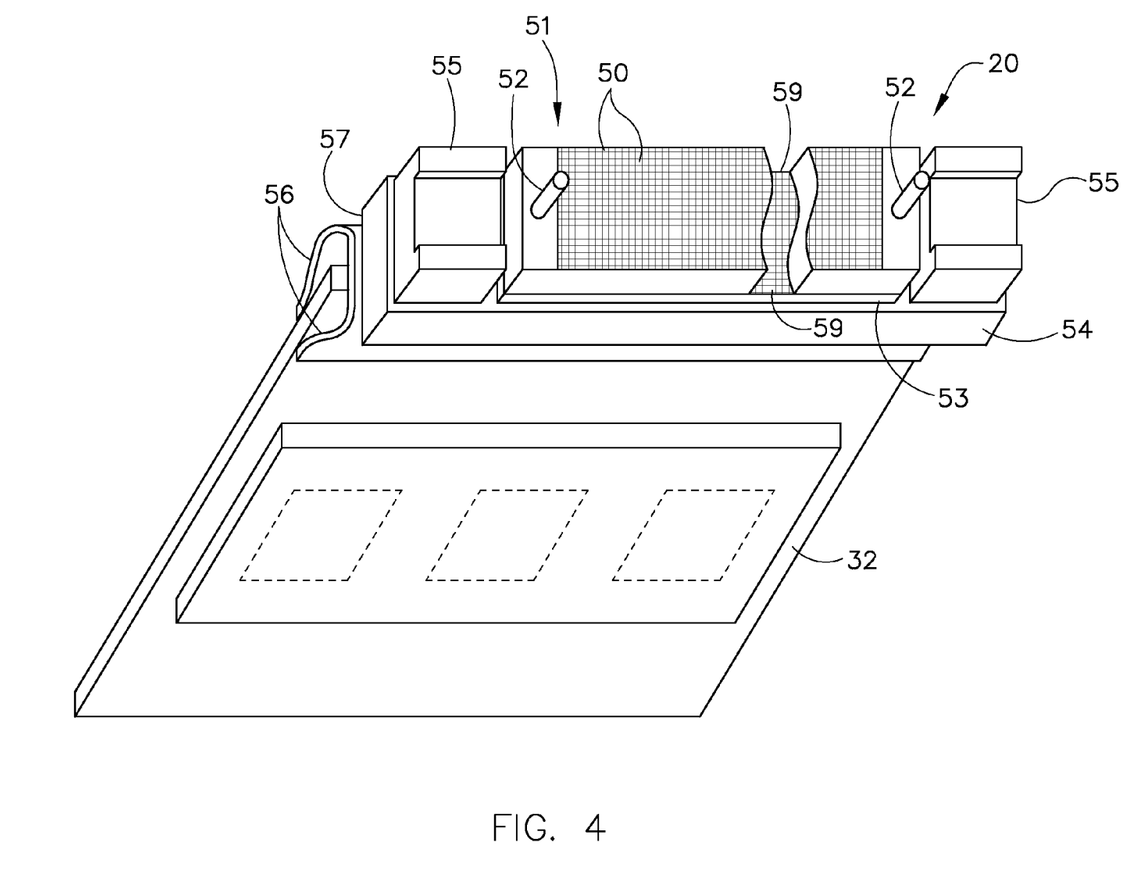
FIG. 4 is a perspective view of one embodiment of a detector.

Referring to FIG. 4, detector 20 includes DAS 32, with each detector 20 including a number of detector elements 50 arranged in pack 51. Detectors 20 include pins 52 positioned within pack 51 relative to detector elements 50. Pack 51 is positioned on a backlit diode array 53 having a plurality of diodes 59. Backlit diode array 53 is in turn positioned on multi-layer substrate 54. Spacers 55 are positioned on multi-layer substrate 54. Detector elements 50 are optically coupled to backlit diode array 53, and backlit diode array 53 is in turn electrically coupled to multi-layer substrate 54. Flex circuits 56 are attached to face 57 of multi-layer substrate 54 and to DAS 32. Detectors 20 are positioned within detector assembly 18 by use of pins 52.

In the operation of one embodiment, x-rays impinging within detector elements 50 generate photons which traverse pack 51, thereby generating an analog signal which is detected on a diode within backlit diode array 53. The analog signal generated is carried through multi-layer substrate 54, through flex circuits 56, to DAS 32 wherein the analog signal is converted to a digital signal.

The following discussion refers to an embodiment of the invention that includes high and low kVp projection datasets from a single energy source having a single detector and a single controller. However, it is to be understood that the invention is equally applicable to a broad range of systems that include but are not limited to having two more sources and two or more detectors. In such systems, a single controller may be used for controlling the sources and detectors, or multiple controllers may be used.

Further, the following discussion refers to obtaining low kVp and high kVp projection data, and correcting the low kVp projection data using the high kVp projection data, as will be further described. However, it is to be understood that the invention is generally applicable to correction of data obtained at one kVp by using data obtained at another kVp. For instance, in the following discussion it is assumed that the low kVp data includes a higher level of noise (or worse statistics), that can lead to image artifacts, than the high kVp data, and thus the high kVp data is used to correct the low kVp data. But, in instances where lower noise or better statistics are obtained in the low kVp projection data as compared to the obtained high kVp projection data, this invention is likewise applicable thereto, and a high frequency component of, or statistics from, the low kVp projection data, in this example, could equally be used to correct for high noise and/or poor statistics in the high kVp projection data.

Figure 5:
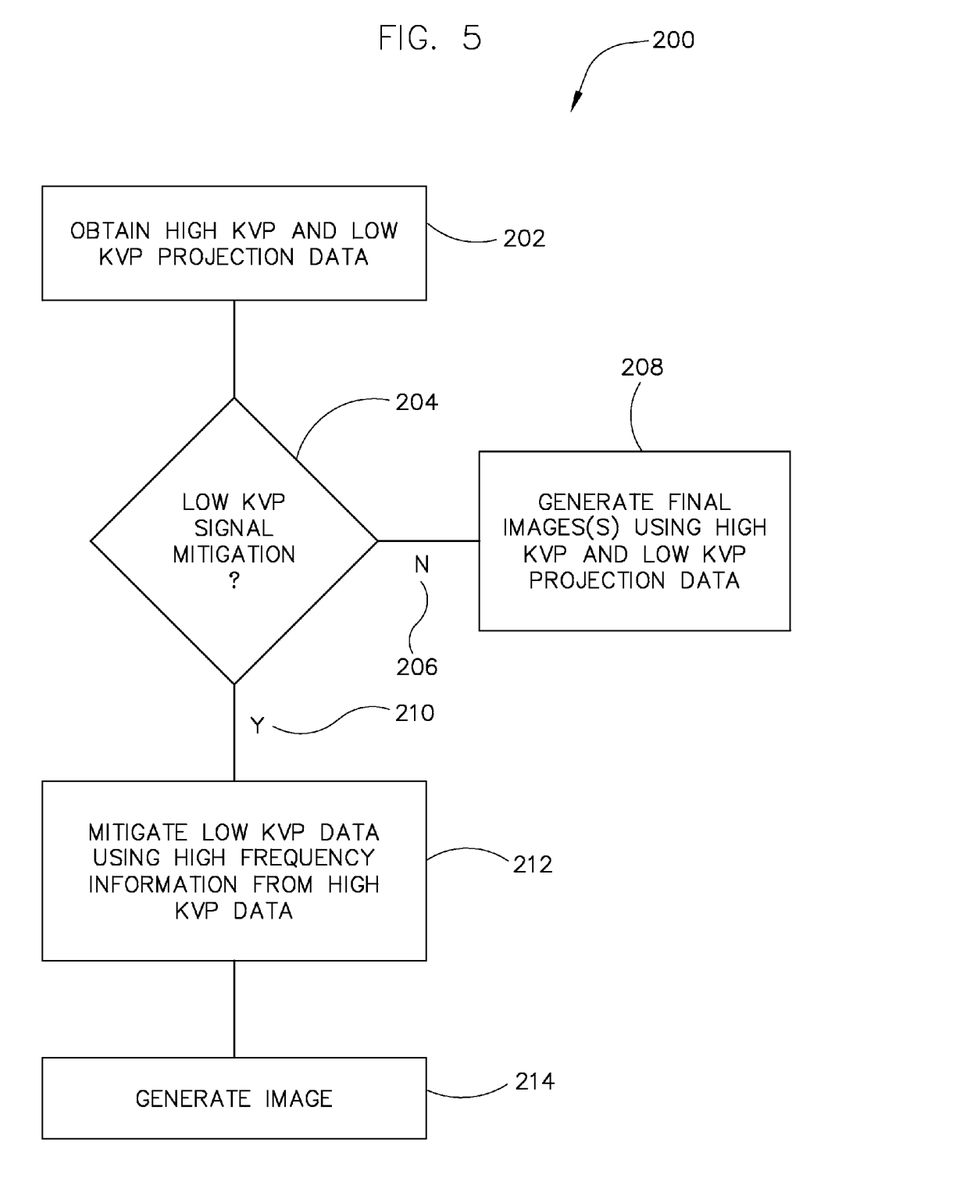
FIG. 5 is a flowchart for adjusting low kVp data according to an embodiment of the invention.

Referring to FIG. 5, a technique 200 for acquiring and mitigating low kVp CT imaging data is shown. Technique 200 includes acquiring high and low kVp projection data or datasets at step 202 using, for instance, generator 29 of FIG. 2 to energize source 14, and determining at step 204 whether to apply a low kVp signal mitigation or correction step, according to embodiments of the invention. The determination at step 204 may be objectively based on a low signal threshold (LST) value, system characteristics, image acquisition settings, and the like. Alternatively, the determination at step 204 may be subjectively based on a user observation when, for instance, streaking or other artifacts are observed in final images.

If no mitigation or correction step is to be applied 206, then final images are generated at step 208 using the high and kVp projection data acquired at step 202. However, if mitigation or correction is to be applied 210, then high frequency data from high kVp projection data is used to mitigate low kVp projection data at step 212, as will be further illustrated in FIG. 6. A dual-energy image is generated at step 214 using the acquired high kVp projection data and the adjusted low kVp projection data, according to known methods for dual-energy image reconstruction.

Figure 6:
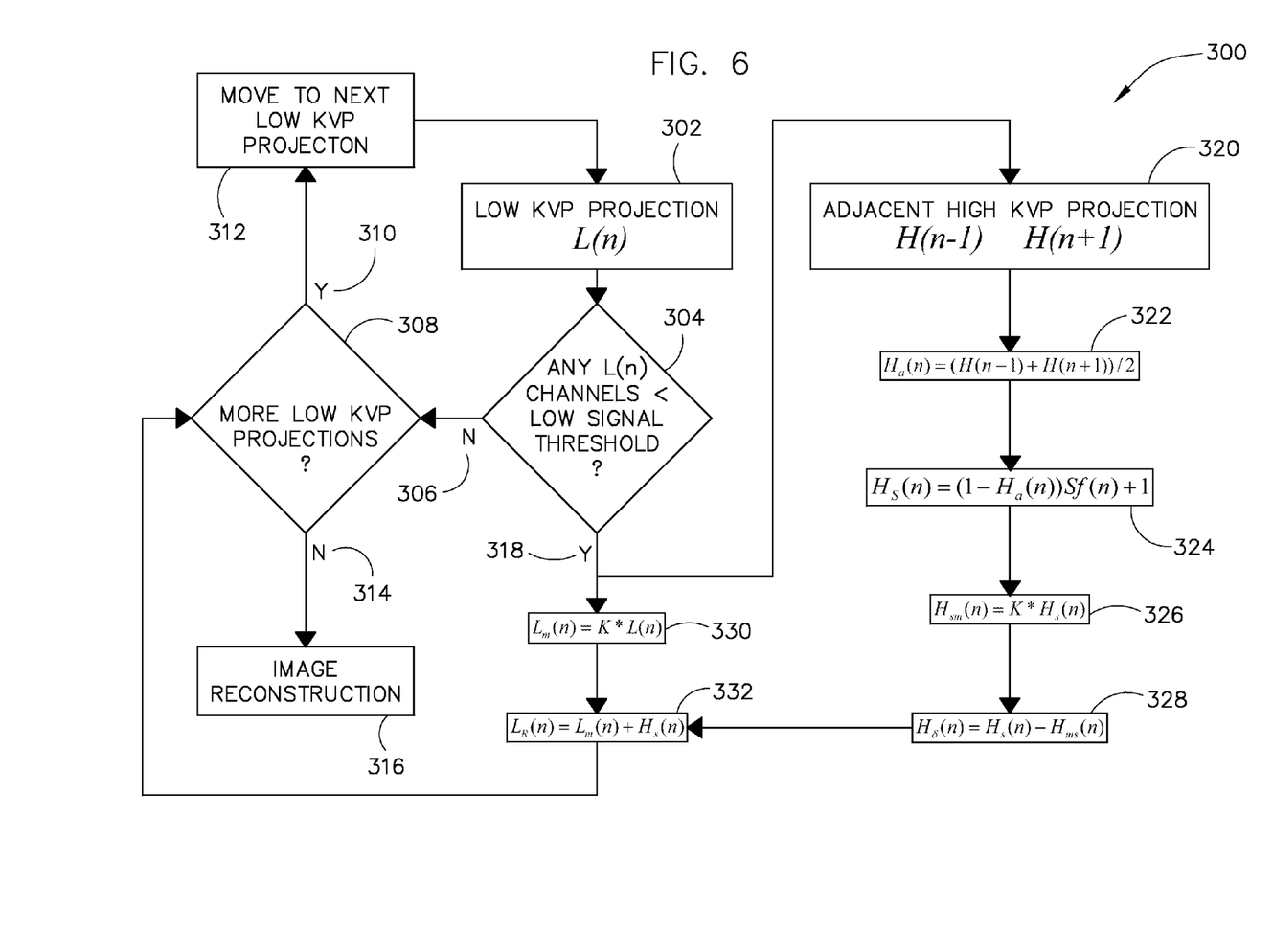
FIG. 6 is a flowchart for adjusting low kVp data according to an embodiment of the invention.

Once it has been determined to mitigate low kVp data at step 210 of FIG. 5, then high frequency resolutions patterns are extracted from high kVp projections and added to acquired low kVp projections, according to embodiments of the invention. According to one embodiment, as illustrated in FIG. 6, low kVp signal resolution is enhanced or mitigated by using neighboring high kVp projection data. In this embodiment, channels of low kVp projections are assessed against an LST and, if one or more channels is below the LST, then adjacent high kVp projections are combined and a high frequency component is extracted therefrom. In one embodiment, the LST is defined as a point wherein low signal corruption begins, and may be empirically determined relative to a basis phantom and based on operating conditions. For instance, the LST may be determined based on one or more parameters such as a number of views per rotation, focal spot wobble, gantry rotation period, geometric efficiency, component geometry (i.e., source, detector, etc.), detector light output, DAS efficiency, DAS electronic noise, kVp, mA, or the like.

Thus, FIG. 6 represents a loop 300 for low kVp data mitigation that begins at step 302, where a low kVp projection is identified for possible mitigation. At step 304, channels of the identified low kVp projection are assessed against an LST. If not below the LST 306, then a query is made at step 308 as to whether more low kVp datasets should be assessed. If so 310, then the next low kVp projection dataset is considered at step 312. However, if all low kVp projections have been assessed and there are none remaining for consideration 314, then an image is reconstructed using high kVp data and the mitigated low kVp data at step 316 as discussed with respect to FIG. 5 at step 214.

Low kVp data may be mitigated as further illustrated in FIG. 6. Thus, when assessing low kVp projection data against the LST, as stated, if one or more channels of the low kVp dataset is below the LST 318, then the low kVp projection dataset is corrected, using high frequency data extracted from the high kVp projection data H(n), according to an embodiment of the invention.

Thus, according to this embodiment, H(n−1) and H(n+1) are determined at step 320 that are adjacent to the low kVp projection data L(n) that is to be mitigated. An average or weighted average high kVp projection $H_a(n)$ is determined at step 322 using:

$$H_a(n)=(H(n-1)+H(n+1))/2; \quad \text{Eqn. 1.}$$

A scaled high kVp projection, $H_s(n)$ is determined at step 324 using the average or weighted average high kVp projection $H_a(n)$:

$$H_s(n)=(1-H_a(n))*Sf(n)+1; \quad \text{Eqn. 2.}$$

The invention applies to averaging of data, whether the averaging is simple averaging or by weighted averaging. Averaging typically includes simple averaging of data, whereas a weighted average includes averaging data with non-equal weighting, as is understood in the art. In other words, as is understood in the art, some data may be weighted more than others. However and regardless, both weighted and non-weighted averaging are included within embodiments of the invention and are encompassed when referring to any type of averaging.

Scaling factor Sf(n) may be determined by a variety of methods, and will be further illustrated below, according to embodiments of the invention. A filtered high kVp projection $H_{sm}(n)$ is formed at step 326 by filtering out high frequency components from the scaled high kVp projection, $H_s(n)$. High frequencies are extracted at step 328 from the scaled high kVp projection, $H_s(n)$ by subtracting the filtered high kVp projection $H_{sm}(n)$ therefrom, to form a high frequency projection $H_\delta(n)$:

$$H_\delta(n)=H_s(n)-H_{sm}(n); \quad \text{Eqn. 3.}$$

Filtered or base low kVp projection data $L_m(n)$ is formed at step 330 by filtering out high frequency components from the low kVp projection data L(n). Once filtered, high frequency data $H_\delta(n)$ is added to the filtered low kVp projection $L_m(n)$ to form a low kVp projection for reconstruction, $L_R(n)$, at step 332:

$$L_R(n)=L_m(n)+H_\delta(n); \quad \text{Eqn. 4.}$$

Scaling factor Sf(n) may be determined by a variety of methods. According to one embodiment, an average or weighted average scaling factor Sf(n) is determined by using both a mean low kVp projection, $L_M(n)$, as determined from the low kVp projection L(n), and the averaged or weighted average high kVp projection, $H_a(n)$ (as determined above):

$$Sf(n) = \frac{\sum 1-L_M(n)}{\sum 1-H_a(a)}; \quad \text{Eqn. 5}$$

Figure 7:
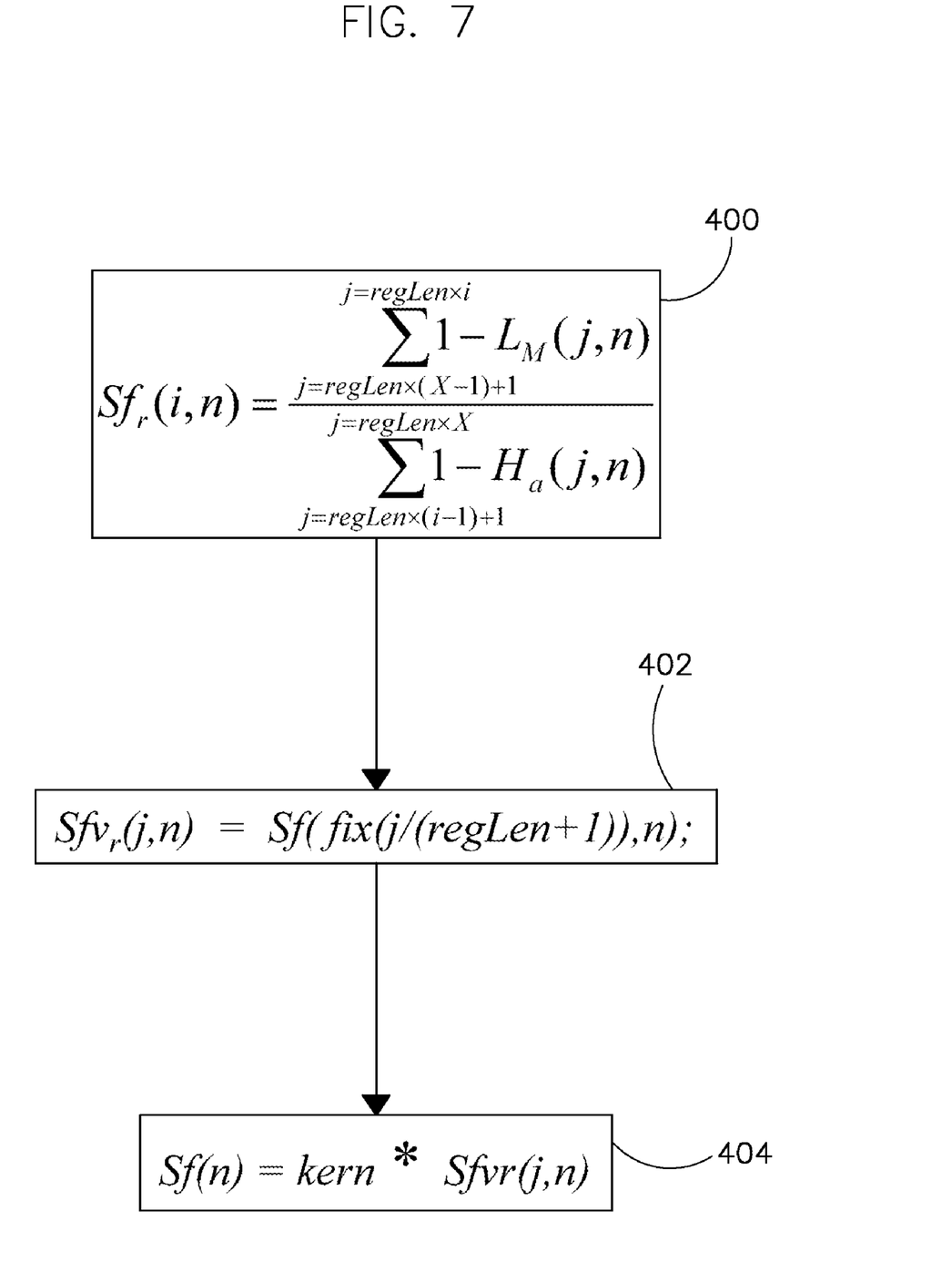
FIG. 7 is a flowchart for determining local region projection scaling according to an embodiment of the invention.

According to another embodiment, scaling factor Sf(n) is determined over a local bin or sub-region. According to this embodiment, a method of determining scaling factor Sf(n) includes calculating a local scale factor for regions of channel bins (for example 75 wide), and creating a channel dependent scale factor vector and low pass filtering the scale factor vector (for example with a 150 point wide hanning kernel). The example is based on a 71 channel single dimensional low pass signal correction filter. Thus, referring to FIG. 7, at step 400 a local region scaling factor $Sf_r$ is determined for regions of channel bins, a channel dependent scale factor having constant values is created in accordance with $Sf_r(j,n)$ within each sub-region bin at step 402, and the scale factor is low pass filtered at step 404 using, for instance, a 50 point hanning kernel.

In order to further minimize or mitigate the effects of low signal in low kVp CT imaging data, high and low kVp projection data may be obtained in such a fashion that may reduce the need to mitigate the acquired data using either a conventional or known low signal mitigation scheme, or by using a scheme such as is illustrated in FIG. 5 above. According to one method, high and low kVp projection data may be acquired in asymmetric sampling intervals such that the low kVp integration period is greater than the high kVp integration period. Thus, referring to FIG. 8, a generator, such as generator 29 of FIGS. 1 and 2, may be configured to output low and high kVp 450. Low kVp 452 is output for a first period 454, and high kVp 456 is output for a second period 458. As illustrated, first period 454 occurs for a time period that is greater than second time period 458. Actual or achieved kVp output includes resulting fall times 468 and rise times 470 due to the capacitance of the system and other known effects.

Figure 8:
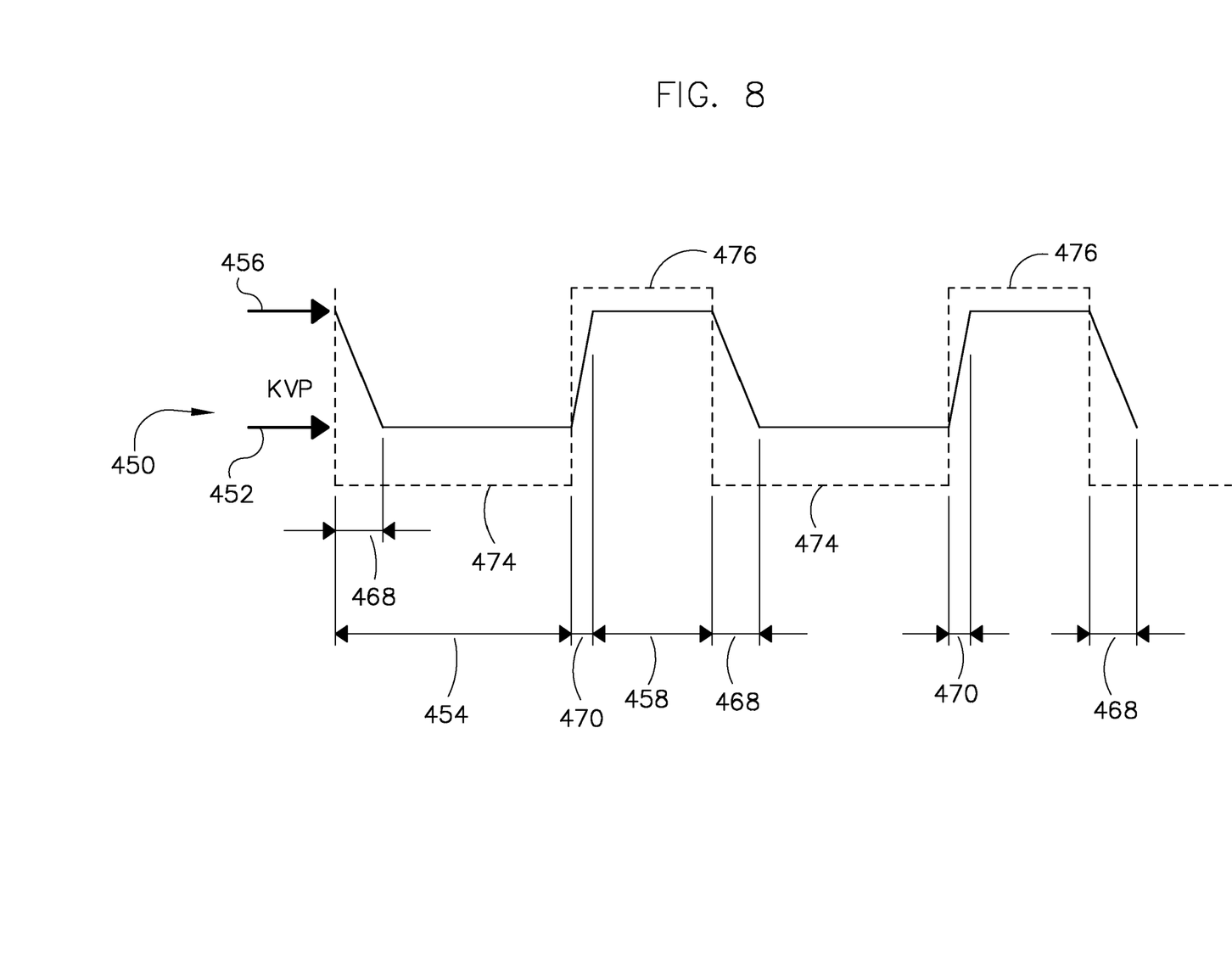
FIG. 8 is an illustration of obtaining low kVp and high kVp projection data according to an embodiment of the invention.

Correspondingly, low and high kVp integration includes low kVp integration periods 474 and high kVp integration periods 476, which are caused to trigger in conjunction with switching from low kVp to high kVp, and vice versa. As such, integration of the low kVp signal occurs for a time period that is greater than a time period of integration of the high kVp signal. This allows more x-ray photons to be captured and integrated per sample, thereby increasing the desired detected signal above, for instance, electronic noise. In one embodiment, improvement may be realized by asymmetrically combining fixed trigger intervals. In one example, data may be sequentially and symmetrically acquired during, for instance, three fixed sample intervals at low kVp and then sequentially during two fixed sample intervals at high kVp. However, sampling in view addition or symmetrical schemes effectively increases the noise floor. As such, according to embodiments of the invention, low and high kVp integration periods 474, 476 include asymmetrically acquired data, as will be discussed. It is to be understood that signal and cost optimization may be realized by combining embodiments and assessing tradeoffs accordingly. As one example, total low kVp integration may be set for a time period that exceeds high kVp integration, but such may include symmetrically acquired data, as will be described below. As such, the noise benefit of extended integration at low kVp may be offset to an extent by symmetrically obtaining such data.

Thus, when data is acquired having asymmetric time intervals or with multiple/sequential low kVp shots and subsequently multiple/sequential high kVp shots, then embodiments of the invention include weighting the acquired projection data to account for the corresponding locations of the gantry, as understood in the art. For instance, when determining neighboring high kVp projection data at step 320, and subsequently averaging the acquired data as described with respect to Eqn. 1 above, then Eqn. 1 is appropriately modified by weighting the neighboring high kVp projections H(n−1) and H(n+1) to account for the asymmetry of the acquired data. Further, one skilled in the art will recognize that multiple neighboring high kVp projections may be used to obtain the average or weighted average high kVp projection $H_a(n)$ at step 322.

Yet another method that can be used independently or in conjunction with any of the disclosed methods and techniques herein is to increase the low kVp integration interval by decreasing the number of projections. This can be done while taking into account and optimizing for azimuthal resolution loss and view aliasing.

Further, it is possible to determine from scout data when projections are likely to be compromised. In one embodiment, orthogonal scan projection data is acquired for both lateral and anterior-posterior (AP) scout scans. After accounting for bowtie attenuation, for each Z-width covered per rotation, view averages may be obtained and separated into center and edge zones. A projection measure (PM) (attenuation in terms normalized to water) is compared to a low signal threshold (LST) that is a function of operating conditions for the scanner. In embodiments of the invention, patient attenuation and LST can be stated directly in terms of pre-log signal intensity or by using post log PM and LST. Accordingly, using both the lateral and the AP scout scans, and LST-PM can be determined for respective lateral and AP views and, if a LST-PM is below a set limit, then a reduced view rate in corresponding sections or views may be used.

In the above discussion, it should be understood that "low kVp" data is a general terminology to describe the projection dataset having worse statistics during a dual energy acquisition. For example, in a dual tube-detector configuration (two sets of tube-detector pairs that are offset by roughly 90-degree angle, as an example), additional filtration can be applied to the high kVp tube-detector (e.g., additional Sn filter for 140 kVp setting) and increased low kVp for the other tube-detector pair (e.g., increase from 80 kVp to 100 kVp). However, as stated, it is possible that the dataset with lower kVp setting (100 kVp) has lower noise than the higher kVp setting (140 kVp). In this case, the correction approach outlined above is applied to the higher kVp setting (140 kVp) instead of the lower kVp setting (100 kVp).

It should also be understood that the process outlined above (low-pass filtering of the "low kVp" data and addition of the high-pass filtered "high kVp" data) is for illustration purpose to demonstrate the leverage of "high kVp" information to correct for "low kVp" deficiencies. However, other approaches can be used to correct for such deficiencies, according to the invention. For example, for "low kVp" channels that exhibit significant noise, we could fit corresponding "high kVp" channels to "low kVp" channels to obtain an estimation of erroneous "low kVp" channels. To be more specific, if a channel k of the "low kVp" channel does not pass a threshold test, nearby channels from k−n to k+n of the "high kVp" data may be used to perform a polynomial fit of the "low kVp" data from k−n to k+n to obtain an estimation of "low kVp" channel k with a fitted "high kVp" channel k.

It should also be understood that filtration parameters (e.g., both high-pass and low-pass described in FIG. 6) can be changed dynamically dependent on measured projection data.

Figure 9:
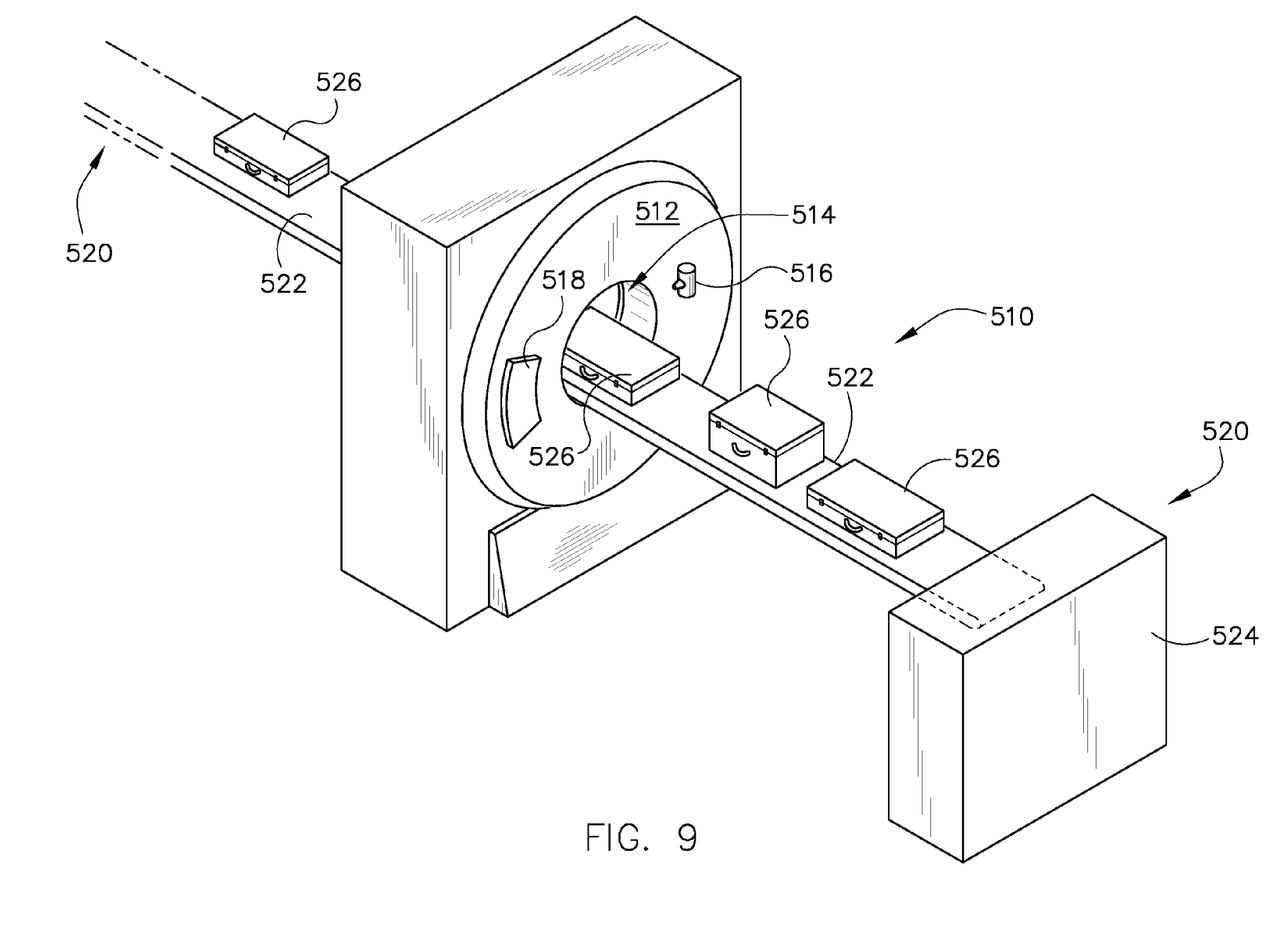
FIG. 9 is a pictorial view of a CT system for use with a non-invasive package inspection system according to an embodiment of the invention.

Referring now to FIG. 9, package/baggage inspection system 510 includes a rotatable gantry 512 having an opening 514 therein through which packages or pieces of baggage may pass. The rotatable gantry 512 houses a high frequency electromagnetic energy source 516 as well as a detector assembly 518 having scintillator arrays comprised of scintillator cells similar to that shown in FIG. 4. A conveyor system 520 also is provided and includes a conveyor belt 522 supported by structure 524 to automatically and continuously pass packages or baggage pieces 526 through opening 514 to be scanned. Objects 526 are fed through opening 514 by conveyor belt 522, imaging data is then acquired, and the conveyor belt 522 removes the packages 526 from opening 514 in a controlled and continuous manner. As a result, postal inspectors, baggage handlers, and other security personnel may non-invasively inspect the contents of packages 526 for explosives, knives, guns, contraband, etc.

Figure 10:
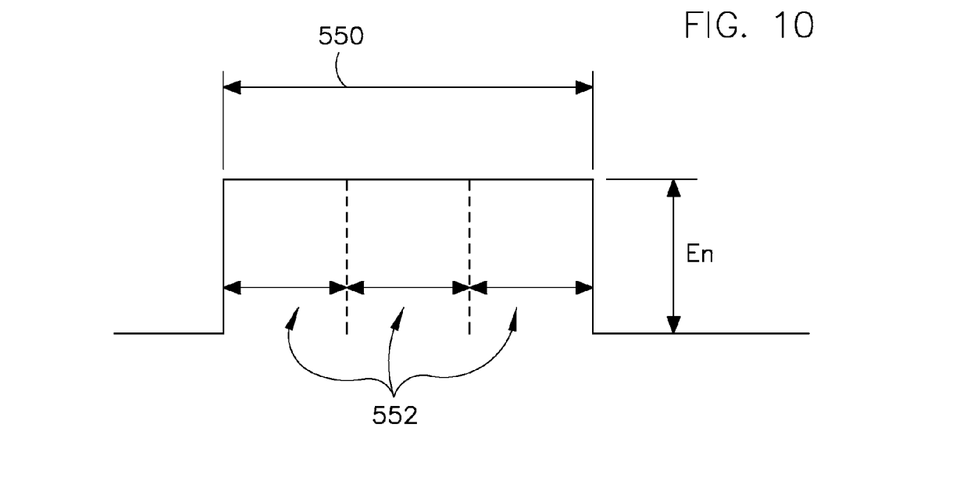
FIG. 10 is an illustration of an asymmetric sampling interval and corresponding symmetric sampling intervals.
Figure 11:
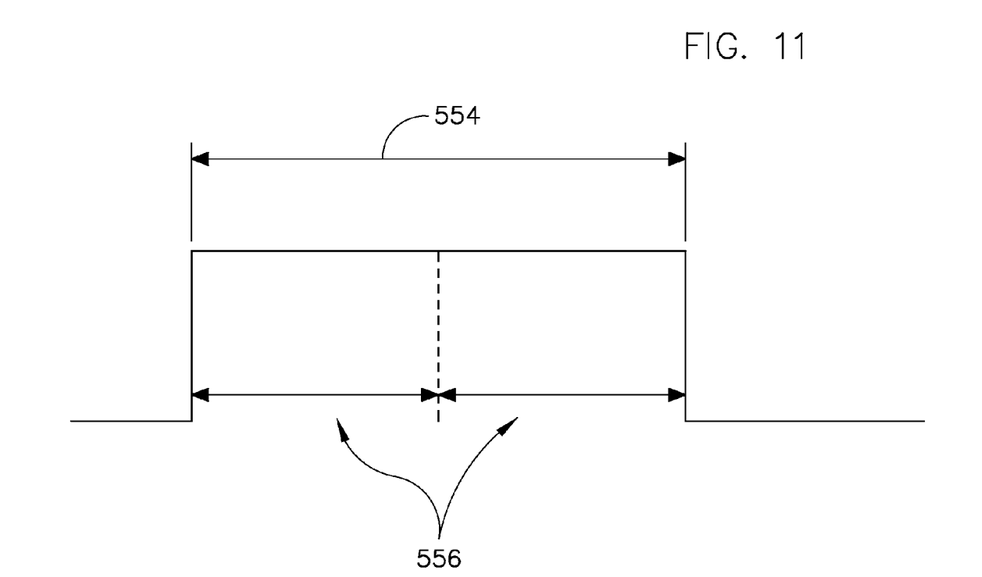
FIG. 11 is an illustration of an asymmetric sampling interval and corresponding symmetric sampling intervals.

As discussed, multi-energy data may be acquired during symmetric or asymmetric sampling intervals. In general, view data may be symmetrically acquired and combined to generate imaging data at a given kVp. For instance, an integration period may be divided into three symmetric windows (FIG. 10) or into two symmetric windows (FIG. 11), as examples. However, when combining such symmetrically obtained views of data, electronic noise (En) compounds proportionally to the square root of the number of view datasets that are being combined:

$$\text{Noise} \propto \sqrt{\#\text{views} * E_n};\quad \text{Eqn. 6.}$$

In other words, in one example, if an integration period includes a combination of three view datasets, then electronic noise during this integration period is compounded by a factor of $\sqrt{3}$, which equals approximately 1.7. Similarly, in another example, if any integration period includes a combination of two view datasets, then electronic noise during this integration period is compounded by a factor of $\sqrt{2}$, which is approximately 1.4. The symmetric intervals will be described and illustrated with respect to FIGS. 10 and 11.

Referring now to FIGS. 10 and 11, sampling intervals comprising both symmetric and asymmetric are illustrated. In a first example shown in FIG. 10, an integration period 550 is a period for image data integration that may correspond to, for instance, low kVp integration period 474 or high kVp integration period 476 of FIG. 8. As stated, for an integration period having electronic noise En and three symmetric view datasets, the total electronic noise N is thus approximately 1.7 times the electronic noise or approximately 1.7×En. Conversely, still referring to FIG. 10, image data may be acquired asymmetrically, according to embodiments of the invention. That is, a single set of view data may be obtained or sampled during integration period 550. Alternatively, data may be sampled or integrated in a symmetric arrangement. In a symmetric arrangement, view data may be acquired during three distinct and symmetric view windows 552. Each set of view data includes a corresponding level of electronic noise En.

In the second example in FIG. 11, an integration period 554 may correspond to low kVp integration period 474 or high kVp integration period 476, as illustrated in FIG. 8. As stated, for an integration period having electronic noise En and two symmetric view datasets, total electronic noise N is thus approximately 1.4 times the electronic noise, thus equals approximately 1.4×En. Conversely, still referring to FIG. 11, image data may be acquired asymmetrically, according to the invention. That is, a single set of view data may be obtained or sampled during a low kVp integration period that may correspond to, for instance, low kVp integration period 474 or high kVp integration period 476 of FIG. 8. Integration period 554 may be integrated in a symmetrical arrangement or an asymmetric arrangement, both of which are illustrated for discussion purposes. In a symmetric arrangement, view data may be acquired during two distinct view windows 556. Each view dataset includes a corresponding level of electronic noise En.

Because the asymmetric acquisition corresponds to a single set of view data acquired during each integration period, there is no compounding effect of electronic noise as was described in the symmetric illustrations as discussed with respect to FIGS. 10 and 11. Thus, according to one embodiment of the invention, a single set of view data may be asymmetrically acquired by integrating imaging signals for each respective low kVp and high kVp period. Because the effect of noise is typically of greater significance during a low kVp integration period (that is, SNR is potentially more compromised at low kVp than at high kVp as a result of electronic noise), embodiments of the invention may include symmetrically acquiring data during, for instance, a high kVp integration period, and asymmetrically acquiring data during a low kVp integration period.

As understood in the art, a longer integration period may affect image resolution to an extent when obtaining CT data. However, in some imaging applications, the image resolution may play a secondary role when considered against image noise. Thus, it is to be understood that asymmetric integration intervals may be selected by optimizing between image noise and image resolution. In one example, for instance, a low kVp signal may range from 3-8 times less than a high kVp signal, hence a low kVp integration period may be 3-8 times greater than a high kVp integration period.

Further, it is to be understood that integration intervals typically include integration during fall times and rise times, such as fall times 468 and rise times 470 as discussed with respect to FIG. 8. For instance, low kVp integration period 474 includes fall time 468, and high kVp integration period 476 includes rise time 470. However, integration during fall and rise times can negatively impact image noise, and it may be desirable to selectively integrate one or both having extended portions of the fall and rise times during, for instance, the high kVp integration periods. In other words, because increased electronic or other noise may be associated with fall and rise times during a multi energy image application, and because SNR tends to be higher during a high kVp period as compared to a low kVp period, it may be desirable to skew the trigger points for integration such that the noise associated therewith is preferably integrated during the high kVp period. Further, fall times and rise times may typically have different time constants, and noise during both may be different. Thus, according to an embodiment, trigger points for high kVp and low kVp integration periods may be triggered independently to best optimize noise against, for instance, image resolution. The trigger points may be selected by determining an amount of skew between a trigger point of a kVp to be applied and a trigger point for acquiring view data. Thus, according to an embodiment of the invention, an amount of rise time skew and fall time skew may be selected based on characteristics of a generator.

Figure 12:
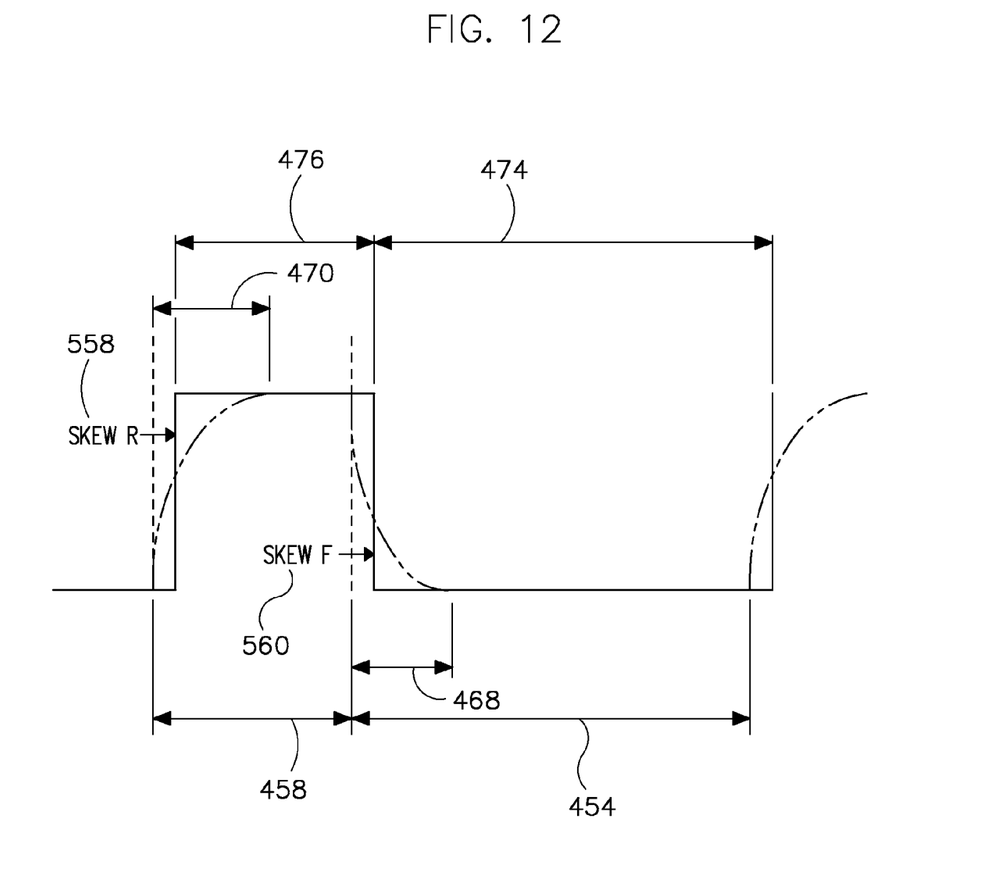
FIG. 12 is a graphical illustration of high and low kVp integration periods having respective lag or skew periods associated therewith.

Referring now to FIG. 12, high and low kVp may be applied, and their respective integration periods skewed therefrom, according to an embodiment of the invention. In order to illustrate this embodiment, that illustrated in FIG. 12 will be discussed with respect to high and low kVp application, rise and fall times, and integration periods as they correspond to respective elements of FIG. 8. FIG. 12 illustrates a first pair of high and low kVp applications and represents a repeating pattern of high and low kVp shots as illustrated in FIG. 8. A low kVp is output for a first period 454, and a high kVp is output for a second period 458. In one embodiment, second period 458 begins at the start of a voltage rise time 470 and ends at the start of a voltage fall time 468. First period 454 begins at the start of voltage fall time 468 and ends at the start of the next voltage rise time 470. The high and low kVp voltages stabilize to steady state after their respective voltage rise time or fall time 470, 468.

Low and high kVp signals may be integrated during respective periods 474, 476. However, in contrast to that illustrated in FIG. 8, low and high kVp integration periods 474, 476 in FIG. 12 may be skewed or offset from the start of rise time 470 and fall time 468 in order to have the noise of the fall and rise times that corresponds to the high kVp be included in the high kVp integrated signal, in one example. In one embodiment, triggering the low and high integration periods 474, 476 may be offset the same amount of time from trigger points where respective low and high kVp is applied via the generator. However, in another embodiment of the invention, the low and high integration periods 474, 476 may be separately controllable by effectively separately controlling a rise time lag or skew period 558 (skew R) and a fall time lag or skew period 560 (skew F), as illustrated. In one embodiment, skew R 558 is set to zero, thus noise associated with rise time 470 is preferably included in the high kVp integration data. One skilled in the art will recognize that both skew R 558 and skew F 560 may be separately controlled in a fashion that minimizes overall noise, according to embodiments of the invention.

Thus, according to embodiments of the invention, data may be asymmetrically obtained in order to minimize overall noise during an integration period. Further, skews during rise and fall times may be selectively and individually controlled in order that noise associated therewith may be preferentially included in the high kVp integration data, according to one embodiment. The skews may be iterated upon, as understood in the art, to optimize noise performance in acquired data and to optimize and balance competing factors that may include noise, resolution, and energy separation, as examples.

An implementation of embodiments of the invention in an example comprises a plurality of components such as one or more of electronic components, hardware components, and/or computer software components. A number of such components can be combined or divided in an implementation of the embodiments of the invention. An exemplary component of an implementation of the embodiments of the invention employs and/or comprises a set and/or series of computer instructions written in or implemented with any of a number of programming languages, as will be appreciated by those skilled in the art.

An implementation of the embodiments of the invention in an example employs one or more computer readable storage media. An example of a computer-readable signal-bearing medium for an implementation of the embodiments of the invention comprises the recordable data storage medium of the image reconstructor 34, and/or the mass storage device 38 of the computer 36. A computer-readable storage medium for an implementation of the embodiments of the invention in an example comprises one or more of a magnetic, electrical, optical, biological, and/or atomic data storage medium. For example, an implementation of the computer-readable signal-bearing medium comprises floppy disks, magnetic tapes, CD-ROMs, DVD-ROMs, hard disk drives, and/or electronic memory.

A technical contribution for the disclosed method and apparatus is that it provides for a computer-implemented apparatus and method of acquiring imaging data at more than one energy range using a multi-energy imaging source.

According to an embodiment of the invention, a CT system includes a rotatable gantry having an opening for receiving an object to be scanned, and a controller configured to apply a first kVp for a first time period, apply a second kVp for a second time period, wherein the second time period is different from the first time period, acquire a first asymmetric view dataset during at least a portion of the first time period, acquire a second asymmetric view dataset during at least a portion of the second time period, and generate an image using the acquired first and second asymmetric view datasets.

According to another embodiment of the invention, a method of imaging includes selecting a rise time skew period based on characteristics of a generator, selecting a fall time skew period, different from the rise time skew period, based on characteristics of the generator, triggering acquisition of a low kVp dataset during a first timeframe and based on the fall time skew period, triggering acquisition of a high kVp dataset during a second timeframe and based on the rise time skew period, wherein the first timeframe is a time duration that is greater than a time duration of the second timeframe, and generating an image using at least the acquired low kVp dataset and the acquired high kVp dataset.

According to yet another embodiment of the invention, a computer readable storage medium having a computer program stored thereon and representing a set of instructions that when executed by a computer causes the computer to optimize an energy separation between imaging data to be acquired at a first energy level and imaging data to be acquired at a second energy level, the optimization based on a rise time characteristic and a fall time characteristic of a generator, acquire a first view of imaging data for at least a portion of a first time period while the first energy level is applied to an imaging source by the generator, acquire a second view of imaging data for at least a portion of a second time period while the second energy level is applied to the imaging source by the generator, and generate an image using the acquired first view of imaging data and the acquired second view of imaging data.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Furthermore, while single energy and dual-energy techniques are discussed above, the invention encompasses approaches with more than two energies. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A CT system comprising:
a rotatable gantry having an opening for receiving an object to be scanned; and
a controller configured to:
apply a first kVp for a first time period;
apply a second kVp for a second time period;
integrate two or more view datasets during the first time period;
integrate one or more view datasets during the second time period, wherein a number of integrated view datasets during the first time period is different from a number of integrated view datasets during the second time period; and
generate an image using the datasets integrated during the first time period and during the second time period.

2. The CT system of claim 1 wherein the first time period is greater than the second time period.

3. The CT system of claim 2 wherein the first kVp is less than the second kVp.

4. The CT system of claim 3 wherein the first kVp is approximately 80 kVp and the second kVp is approximately 140 kVp.

5. The CT system of claim 2 wherein a first set of data is comprised of one of the one or more view datasets integrated during the second time period and wherein the controller is configured to symmetrically obtain a second set of data by being configured to integrate another of the one or more view datasets during the second time period.

6. The CT system of claim 5 wherein the first set of data and the second set of data are acquired during timeframes of approximately equal duration.

7. The CT system of claim 2 wherein an integration period for integrating the two or more view datasets during the first period is 3-8 times greater than an integration period for integrating the one or more view datasets during the second time period.

8. The CT system of claim 2 wherein the controller is configured to asymmetrically acquire data by being configured to integrate all of the view datasets during the first time period and at the first kVp and to integrate all of the view datasets during the second time period and at the second kVp.

9. A method of imaging, the method comprising:
integrating two or more view datasets that are obtained using a CT scanner for a first time period and while the CT scanner causes an x-ray source thereof to apply a first kVp;
integrating a first of one or more view datasets that are obtained using the CT scanner during a second time period and while the CT scanner causes the x-ray source thereof to apply a second kVp, wherein a number of view datasets integrated during the first time period is different from a number of view datasets integrated during the second time period; and
generating an image using the integrated two or more view datasets from the first time period and using the integrated first of the one or more view datasets from the second time period.

10. The method of claim 9 comprising asymmetrically integrating all of the view datasets during the first time period to form a first kVp dataset, and integrating all of the view datasets during the second time period to form a second kVp dataset.

11. The method of claim 9 comprising symmetrically integrating a second of the one or more view datasets that are obtained using the CT scanner during the second time period and while the CT scanner causes the x-ray source thereof to apply the second kVp.

12. The method of claim 11 wherein an integration period for integrating the first of the one or more view datasets and an integration period for integrating the second of the one or more view datasets are approximately of equal duration.

13. The method of claim 9 wherein the first time period is greater than the second time period and wherein the second kVp is greater than the first kVp.

14. A computer readable storage medium having a computer program stored thereon and representing a set of instructions that when executed by a computer causes the computer to:

apply a first kVp for a first time period to an x-ray source in a CT system;
apply a second kVp for a second time period to the x-ray source;
integrate two or more view datasets obtained during the first time period;
integrate one or more view datasets obtained during the second time period, wherein a number of integrated view datasets during the first time period is different from a number of integrated view datasets during the second time period; and
generate an image using the datasets obtained during the first time period and during the second time period.

15. The computer readable storage medium of claim 14 wherein the instructions cause the computer to asymmetrically integrate all of the view datasets obtained during the first time period to form a first kVp dataset and to integrate all of the view datasets obtained during the second time period to form a second kVp dataset.

16. The computer readable storage medium of claim 14 wherein the instructions cause the computer to symmetrically integrate a second of the one or more view datasets obtained during the second time period.

17. The computer readable storage medium of claim 16 wherein the instructions cause the computer to integrate the first of the one or more view datasets and the second of the one or more view datasets for approximately an equal time duration.

18. The computer readable storage medium of claim 14 wherein the first time period is approximately 3-8 times greater than the second time period.

19. The computer readable storage medium of claim 14 wherein the first kVp is less than the second kVp.

20. The computer readable storage medium of claim 19 wherein the first kVp is approximately 80 kVp and the second kVp is approximately 140 kVp.

* * * * *